US00PP31380P3

(12) United States Plant Patent
Slaughter et al.

(10) Patent No.: US PP31,380 P3
(45) Date of Patent: Jan. 21, 2020

(54) PEACH TREE NAMED 'BURPEACHFORTYTWO'

(50) Latin Name: *Prunus persica*
Varietal Denomination: Burpeachfortytwo

(71) Applicant: WAWONA PACKING CO., LLC, Cutler, CA (US)

(72) Inventors: John K. Slaughter, Fresno, CA (US); Timothy J. Gerdts, Kingsburg, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 15/932,485

(22) Filed: Mar. 6, 2018

(65) Prior Publication Data

US 2019/0281741 P1 Sep. 12, 2019

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 6/7463; A01H 5/08
See application file for complete search history.

*Primary Examiner* — Keith O. Robinson
(74) *Attorney, Agent, or Firm* — Potter Anderson and Corroon LLP

(57) ABSTRACT

A new and distinct variety of peach tree (*Prunus persica*), which is denominated varietally as 'Burpeachfortytwo', and which produces an attractively colored white-fleshed, clingstone peach which is mature for harvesting and shipment approximately September 5 to September 10 under the ecological conditions prevailing in the San Joaquin Valley of central California.

1 Drawing Sheet

Botanical designation: *'Prunus persica'*.
Varietal denomination: 'Burpeachfortytwo'.

BACKGROUND OF THE NEW VARIETY

The present variety of peach tree resulted from an ongoing program of fruit and nut tree breeding. The purpose of this program is to improve the commercial quality of deciduous fruit and nut varieties, and rootstocks, by creating and releasing promising selections of *Prunus, Malus, Punica*, and *Juglans* species. To this end we make both controlled and hybrid cross pollinations each year in order to produce seedling populations from which improved progenies are evaluated and selected.

The seedling, 'Burpeachfortytwo' was originated by us, and selected from a population of seedlings growing in our experimental orchards which are located near Fowler, Calif. The seedlings, grown on their own roots, were derived from planting seed of an open pollinated seedling which was identified as, 'A40.005', (unpatented), and which further produces a yellow-fleshed, acidic fleshed peach. The pollen parent of this open pollinated seedling is known and unnamed, (unpatented), and produces a white-fleshed, clingstone, low acid nectarine. The resulting fruit was collected from the female parent ('A40.005') at a mature stage, and then seeds were extracted in September of 1998. After a period of stratification, the seed was placed in the greenhouse, by population, and then field planted for tree establishment, and ultimately to exhibit fruit for evaluation. One peach seedling which produced white-fleshed fruit, and which further is the present variety, exhibited especially desirable characteristics, and was then designated as 'E63.008'. This seedling was marked for subsequent observation. After the 2001 fruiting season, the new variety of peach tree was selected for advanced evaluation, and repropagation.

ASEXUAL REPRODUCTION

Asexual reproduction of this new and distinct variety of peach tree was accomplished by budding the new peach tree onto 'Nemaguard' Rootstock (un-patented). This was performed by us in our employer's experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burpeachfortytwo' is a new, novel, and distinct variety of peach tree. The present, new variety is a regular, and productive, bearer of relatively large, firm, white-fleshed, low acid, and clingstone fruit which have a very good flavor, and eating qualities. This new peach tree has what is considered to be a medium chilling requirement of approximately 650 hours. Further, the present, new variety produces relatively uniformly sized fruit throughout the tree's canopy. In addition to the foregoing, the fruit of the new peach also appears to have what are considered to be good handling and shipping qualities. The 'Burpeachfortytwo' peach tree bears fruit which are typically ripe for commercial harvesting and shipment on approximately September 5 to September 10 under the ecological conditions prevailing in the San Joaquin Valley of central California.

In relative comparison to the 'Snow King' peach tree (U.S. Plant Pat. No. 8,415), which is the closest known variety, the new variety of peach tree bears fruit of a more rounded and less elongated shape in general and a less pronounced apex. Further, the present, new variety is distinguishable from the 'Snow King' peach tree in view of its fruit, which has a higher percentage of reddish blush on the surface of its skin, whereas the 'Snow King' peach tree produces fruit having a lower percentage of reddish blush on the surface of its skin. Still further, the present, new variety is distinguishable from the 'Snow King' peach tree in view of its fruit, which is a clingstone, whereas the 'Snow King' peach tree produces fruit having a freestone.

In relative comparison to the unpatented seed parent 'A40.005', the current variety is easily and clearly distinguishable because it produces fruit having a white flesh, whereas the seed parent produces fruit have a yellow flesh characteristic. Moreover, the current variety of peach produces fruit having a low acidity, whereas the seed parent produces fruit having high malic acid levels. In relative comparison to the unnamed, and unpatented, pollen parent, the current variety is easily and clearly distinguishable because it is a peach, whereas the pollen parent is a nectarine.

BRIEF DESCRIPTION OF THE DRAWINGS

The accompanying drawing, which is provided, is a color photograph of two whole mature fruit in their fifth year displaying both the apical and basal aspects thereof. One mature fruit bisected transversely through the equatorial plane, and which reveals the flesh color, and stone characteristics thereof. The external coloration of the fruit as shown in the photograph is sufficiently matured for harvesting and shipment. Additionally, the photograph displays a sample vegetative shoot bearing typical leaves. Further, the photograph displays a typical stone with the flesh removed.

The colors in these photographs are as nearly true as is reasonably possible in a color representation of this type. Due to chemical development, processing, and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY:

The following detailed description has been prepared solely to comply with the provisions of 35 U.S.C. § 112, and does not constitute a commercial warranty (either expressed or implied), that the present, new variety will, in the future, display the botanical, horticultural, or other characteristics as set forth, hereinafter. Therefore, this disclosure may not be relied upon to support any future legal claims including, but not limited to, breach of warranty and merchantability, or fitness for any particular purpose, or non-infringement which is directed, in whole, or in part, to the present, new variety.

DETAILED DESCRIPTION

Referring more specifically to the pomological details of this new and distinct variety of peach tree, the following has been observed during the tenth fruiting season, and under the ecological conditions prevailing at the orchards of the assignee which are located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

TREE

Size: Generally considered medium to large in its growth pattern, as compared to other common commercial peach cultivars ripening in the late season of maturity. The tree of the present variety was pruned to a height of approximately 270.0 cm to about 310.0 cm at commercial maturity.

Width: On average, about 285.0 cm.

Vigor: Considered to have a medium vigor. The present peach tree variety grew from about 170.0 cm to about 180.0 cm, in height, during the first growing season. The new variety was pruned to a height of approximately 150.0 cm during the first dormant season, and primary scaffolds were then selected for the desired tree structure.

Productivity: Considered to be productive. Fruit set varies from more than the desired crop load, to levels higher than desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

Fruit bearing: Considered to be regular. Fruit set has been more than adequate during the previous years of observation, and thinning was necessary during the past 17 years on both the original seedling and on subsequent asexually reproduced trees.

Tree form: Considered to be upright, and pruned into a vase shape.

Density: Considered to be moderately dense. It has been discovered that pruning the branches from the center of the tree to obtain a resulting vase shape allows for enhanced air movement, and appropriate amounts of sunlight to improve fruit color, and renewal of fruiting wood throughout the tree.

Hardiness: The present tree was grown and evaluated in USDA Hardiness Zone 9. The calculated winter chilling requirements of the new tree is approximately 650 hours at a temperature below 7.0 degrees C. The present variety is considered to be hardy under typical central San Joaquin Valley climatic conditions.

TRUNK

Diameter: On average, about 25.5 cm in diameter when measured at approximately 15.24 cm above the soil level. This measurement was taken at the end of the 17th growing season.

Bark texture: Considered to be moderately rough, with folds of papery scarfskin being present. Since bark development, and coloration, change with advancing tree age, this characteristic varies with the tree vigor, age, and regional conditions.

Lenticels: Flat, oval lenticels are present. The lenticels range in size from approximately 4.0 mm to about 7.0 mm in width, and between approximately 1.0 mm to about 2.0 mm in height. The development and size of the trunk lenticels can be influenced, to some degree, by the ambient growing conditions. As trees of this variety mature, lenticels are present, but they are generally covered by increasing layers of cork (mature bark) and therefore become less apparent.

Lenticel color: Considered to be an orange brown, (RHS Greyed-Orange Group 164 B).

Bark coloration: Variable, but it is generally considered to be a greyed brown, (RHS Grey-Brown Group N199 B). This bark description was taken from trees in their seventh leaf which have ruptured the scarf skin, and which also have developed bark furrowing which is much more typical of the bark of older trees. It should be noted that the coloration of the bark is influenced, and varies, as the smoother, darker, background color approaches other bark features such as the lenticels, and the initial fissures which form a feature of the scarf skin development.

BRANCHES

Size: Considered to be medium to large for the species.

Diameter: Considered to be average for the species. The branches have a diameter of about 13.0 cm when measured during the 10th year after grafting.

Flowering shoot thickness: On average, about 5.0 mm to about 7.0 mm on annual wood.

Flowering shoot anthocyanin coloration: Absent.

Surface texture: Considered to be average, and appearing relatively smooth but with more furrowing on wood which is several years old.

Crotch angles: Primary branches are considered to be variable, and are usually growing at an angle of about 43 to about 55 degrees when measured from a horizontal plane. This particular characteristic can vary due to the influence of the assorted ecological conditions, and the cultural practices which are being utilized.

Current season shoots:

*Surface texture.*—Substantially glabrous.

Internode length: On average, about 2.4 cm.

Color of mature branches: Grey brown, (RHS Greyed-Orange Group 166 C).

Current season's shoots:

*Color.*—Medium-light green, (RHS Yellow-Green Group 146 C). The color of new shoot tips is considered to be a bright and shiny green (RHS Yellow-Green Group 146 D). The vegetative shoot color can be significantly influenced by plant nutrition, irrigation practices, and exposure to sunlight, and therefore should not be considered a consistent botanical characteristic of this new variety.

LEAVES

Size: Considered to be medium for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient, and other cultural factors listed above.

Leaf length: On average, about 153.0 to about 160.0 mm.

Leaf width: On average, about 32.0 to about 35.0 mm.

Leaf base-shape: From the petiole, the leaf base extends and diverges at even and symmetrical widths. The leaf base shape is not considered a common oblique form of base.

Leaf form: Lanceolate.

Leaf tip form: Acuminate.

Leaf color:

*Upper leaf surface.*—Dark yellowed green, (approximately RHS Yellow-Green Group 147 A).

Leaf texture:

*Upper leaf surface.*—Glabrous.

*Lower leaf surface.*—Glabrous.

Leaf color:

*Lower leaf surface.*—Light to medium green, (approximately RHS Yellow-Green Group 146 A).

Leaf venation: Pinnately veined.

Mid-vein:

*Color.*—Considered a light yellow, (approximately RHS Yellow-Green Group 154 D) in the early to mid-period of the growing season.

Leaf margins: Gently undulating.

*Form.*—Considered finely crenate.

*Uniformity.*—Considered generally uniform.

Leaf petioles:

*Form.*—Considered to be canaliculated, and having a more pronounced trough when viewed from the dorsal aspect. The petiole margin is considered to be rounded when viewed from the ventral aspect.

*Length.*—On average, about 7.0 to about 10.0 mm. Considered to be medium to small for the species.

*Diameter.*—On average, about 1.5 to about 2.0 mm.

*Color.*—Yellow green, (approximately RHS Yellow-Green Group 144 A).

*Texture.*—Virtually glaborous.

*Strength.*—Considered durable for species until senescence.

Leaf glands:

*Size.*—Considered small for the species; on average, about 1.5 mm in length; and on average, about 1.0 mm in height.

*Number.*—Generally, one, and less commonly two, glands appear per marginal side. Observations of more than two glands per marginal side are very uncommon.

*Type.*—Glands located at the base of the leaf are predominantly reniform in shape.

*Color.*—Considered a medium-dark brown, approximately (RHS Brown Group N199 B). Typically, the coloration of the glands darkens, and occasionally begins to desiccate during the mid-late growing season.

Leaf stipules:

*Size.*—Approximately 4.0 mm to 6.5 mm in length, and approximately 1.0 mm to 1.5 mm in width.

*Number.*—Typically, 2 per leaf bud, and up to 6 per shoot tip.

*Form.*—Lanceolate, and having a serrated marginal edge.

*Color.*—Green, (approximately RHS Green Group N138 A) when young, but graduating to a brown color, (approximately RHS Greyed-Orange Group 165 A) with advancing senescence. The leaf stipules are generally considered to be early deciduous.

Leaf bud burst: Leaf burst (enfoliation) is considered very early, initiating approximately February 20 to February 25 under the current growing conditions.

FLOWER BUDS

Hardiness: No winter injury (bud death) has been noted during the last several years of observation in the central San Joaquin Valley. The new variety of peach tree has not been intentionally subjected to drought, cold or heat stress, and therefore this information is not available.

Flower bud:

*Size*.—Variable, and dependent on the state of maturity. The flower buds as described were observed approximately 7 days prior to bloom.

*Length*.—On average, about 16.0 mm.

*Diameter*.—On average, about 7.0 mm.

*Surface texture*.—Pubescent.

*Orientation*.—Considered appressed, but appearing less so as the blossoms near opening.

Bud scale color: Approximately RHS Greyed-Purple N186 C.

FLOWERS

Date of first bloom: Observed on Mar. 1, 2017. The blooming time is considered average in relative comparison to other commercial peach cultivars grown in the central San Joaquin Valley. The date of full bloom was observed on Mar. 5, 2017. The date of full bloom varies slightly with climatic conditions, and prevailing cultural practices.

Duration of bloom: On average, about 8 or more days. This characteristic varies slightly with the prevailing climatic conditions.

Flower class: Considered to be a perfect flower, complete and perigynous.

Flower type: Considered to be rosette (showy).

Flower size: Considered to be medium to large for the species. The flower diameter, at full bloom, is, on average, about 45.0 to 50.0 mm.

Bloom quantity: Considered to be abundant.

Flower bud density: Generally considered to be dense.

Flower bud frequency: Generally, two flower buds appear per node. Occasionally one flower bud per node is observed.

Petal size: Generally considered medium to large for the species.

*Petal length*.—On average, about 24.5 to 26.5 mm.

*Petal width*.—On average, about 18.0 to 21.0 mm.

Petal form: Considered broadly ovate.

Petal count: Nearly always 5.

Petal texture:

*Upper petal texture*.—Gently glaborous.

*Lower petal texture*.—Very gently glaborous.

Petal color: Considered a light pink at the popcorn stage, (RHS Red-Purple Group 65 D), and darkening with advanced senescence, and the exposure of sunlight, to a medium-dark pink, (RHS Red-Purple 63 C).

Fragrance: Considered to be slight.

Petal claw:

*Form*.—Considered to be ovate, generally medium to small, and more elongated and relatively narrower when compared to other varieties.

*Length*.—On average, about 7.0 to 9.0 mm.

*Width*.—On average, about 4.5 to 6.0 mm.

Petal margins: Generally considered to be variable, from nearly smooth to moderately undulate, and ruffled, especially apically.

Petal apex: Often the petal margin exhibits a shallow and wide recess at tip.

*Width*.—On average, about 1.5 to 3.0 mm.

*Depth*.—On average, about 1.0 to 2.0 mm.

Flower pedicel:

*Length*.—Considered to be medium to long with a length of, on average, about 1.5 to about 3.0 mm.

*Diameter*.—On average, about 1.5 mm.

*Color*.—A medium-brown, approximately (RHS Grey-Brown Group N199 D) depending upon the pedicel, fruit maturity, and the timing of the visual observation.

*Strength*.—Tenacious. Considered to be average for the species.

Floral nectaries:

*Color*.—Considered a pale green (approximately RHS Yellow-Green Group 154 B).

Calyx:

*Surface texture*.—Generally glabrous.

*Color*.—A dull orange red, (approximately RHS Greyed-Orange Group N167 B).

Sepals:

*Upper surface texture*.—Pubescent.

*Lower surface texture*.—Glabrous.

*Number*.—5 sepals.

*Size*.—Considered to be average.

*Sepal length*.—On average, about 4.5 to 7.0 mm.

*Sepal width*.—On average, about 5.0 to 6.5 mm.

*Sepal shape*.—Generally obovate.

*Sepal margin*.—Considered to be smooth and entire.

*Sepal color*.—A dull grey-red (approximately RHS Greyed-Red Group 178 B).

Anthers:

*Generally*.—Approximately 1.0 mm to 1.5 mm in length, and approximately 1.0 mm in width.

*Color*.—Orange when viewed dorsally, and prior to dehiscence, (approximately RHS Greyed-Orange Group 168 B).

*Position relative to stigma*.—Generally, the stigma is superior to the anthers by approximately 1.0-2.0 mm.

Pollen production: Pollen is abundant, and has a yellow color, (approximately RHS Yellow-Orange Group 21 B).

Fertility: Self-fertile.

Filaments:

*Size*.—On average, about 16.5 to 19.5 mm in length.

*Color*.—Considered white to a pinkish-white, (RHS Red Purple Group 65 D).

Pistil:

*Number*.—Usually one, and only occasionally more than one.

*Generally*.—Considered to be medium to large in size.

*Length*.—On average, about 16.5 to about 19.5 mm in length including the ovary. Considered to be long for the species.

*Ovary*.—Pubescent.

*Color*.—Considered a very pale green, (approximately RHS Yellow-Green Group 149 D).

*Surface texture*.—Considered to be pubescent.

*Position relative to petals*.—At flower maturity the stamens grow to be superior to the petals.

FRUIT

Maturity when described: Firm ripe condition (shipping ripe).

Date of first picking: Approximately Sep. 2, 2017.

Date of last picking: Sep. 10, 2017. The date of harvest can vary with the prevailing climatic conditions, volume of fruit on the tree, and the current climatic and cultural practices which are employed.

Size: Considered to be large, and very uniform.

Average cheek diameter: On average, about 72.0 to about 79.0 mm.

Average axial diameter: On average, about 73.0 to about 78.0 mm.

Typical weight: On average, about 275.0 grams. This characteristic is quite dependent upon the prevailing cultural practices and growing conditions, and therefore is not particularly distinctive of the new variety.

Fruit form:

*Generally*.—Considered to be globose. The fruit is generally very uniform in symmetry.

Mucron tip: Absent.

Fruit suture: No stitching exists along the suture line.

Suture:

*Color*.—Generally, the fruit appears blushed to the same degree as the skin, (approximately RHS Orange-Red Group N34 A).

Ventral surface:

*Form*.—Considered to be even, and uniform in appearance, when it is viewed from the lateral, sutural plane.

Apex:

*Shape*.—Rounded.

Base:

*Shape*.—Generally smooth.

Stem cavity:

*Generally*.—It extends in a rounded circular form which is generally considered to be uniform. The stem cavity is rounded but slightly extended toward the suture. The depth of the stem cavity is, on average, about 8.0 mm to about 10.0 mm. The width of the stem cavity is, on average, about 30.0 mm. The length of the stem cavity, when measured in the suturial plane, on average, is about 55.0 mm.

Fruit skin:

*Thickness*.—Considered to be medium in thickness, and tenacious to the flesh.

*Surface texture*.—Short, fine, and pubescent. The pubescence is moderately abundant.

*Taste*.—Non-astringent.

*Tendency to crack*.—Not observed in the previous years of observation and evaluation.

Fruit skin color:

*Blush color*.—Generally speaking, a red blush exists on a majority of the skin of the fruit (approximately RHS Orange-Red Group N34 A), and is more typically present on the portions of the fruit facing the sunlight. The blush of the fruit typically covers approximately 65%-85% of the fruit skin surface. The percentage of the blush on the fruit skin surface can vary, and is generally dependent upon the influences of the current season's environmental conditions, the fruit's exposure to direct sunlight, the specific fruit maturity, and also the prevailing ecological and cultural conditions under which the fruit was grown.

Ground color: A creamy white, (approximately RHS Yellow-White Group 158 C). The ground color of the fruit can vary significantly based upon the maturity of the fruit when this measurement is taken, and generally gains a lighter, and less green cast (approximately RHS Yellow-Green Group 145 D), with higher maturity.

Fruit glossiness: Fruit is not considered to be glossy.

Fruit stem:

*Size*.—Considered medium in length, on average, about 6.0 to about 8.0 mm.

*Diameter*.—On average, about 2.0 to about 3.0 mm.

*Color*.—Pale yellow-green, (approximately RHS Yellow-Green Group N144 C).

Fruit flesh:

*Ripening*.—Considered to be even.

*Texture*.—Firm, juicy, and dense. Considered to be firm, yet non-melting.

*Fibers*.—Considered to be absent or weak.

*Aroma*.—Considered to be light.

*Eating quality*.—Considered to be very good.

*Flavor*.—Considered balanced with sweetness and acidity.

*Juice production*.—Moderate.

*Brix*.—About 15.0 to 18.0 degrees. This characteristic varies slightly with the number of fruit per tree, the maturity of fruit when harvested, the prevailing cultural practices, and the ambient climatic conditions.

*Acidity*.—Considered to be low. Approximately 0.3 titratable acidity. Acid levels assayed from fruit flesh can vary with fruit maturity, sunlight exposure, climatic, and other regional and cultural influences.

*Flesh color*.—Considered to be a cream white, (approximately RHS Yellow Group 13 C), often exhibiting pigmentation of red radiating from the stone (approximately RHS Greyed-Red Group 179 A).

STONE

Type: Considered a clingstone.

Size: Considered to be medium for the species. The stone size varies significantly depending upon the tree vigor, the crop load, and the prevailing growing and cultural conditions under which the tree was grown.

Length: On average, about 29.0 to about 31.0 mm.

Width: On average, about 22.0 to about 26.0 mm.

Diameter: On average, about 18.0 to about 20.0 mm.

Form: Roughly obovate.

Stone base:

*Shape*.—Shortly attenuate.

Apex:

*Shape*.—The stone exhibits a slight to prominently acute apex.

Stone surface:

*Surface texture*.—Considered to be irregularly furrowed toward the apex. Further, more pitting exists in the mid-portion of the stone (laterally), and is more common toward the base.

*Ridges*.—Ridging is generally more prominent, and is usually oriented parallel, and laterally relative to the ventral and dorsal margins.

*Ventral edge*.—The ventral edge is generally considered to be troughed with three substantial grooves that converge apically.

*Dorsal edge*.—Shape: Generally considered to be even. The folds of the surface ridges appearing on the external margins often end gently along the suture.

Stone color: The color of a mature, dry stone is generally considered a dull brown, approximately (RHS Greyed-Orange Group 177 A). The stone color can vary considerably in view of how recently the fruit has ripened, the degree of oxidation which has taken place, and any blanching which has occurred due to exposure of the stone to sunlight.

Tendency to split: Splitting has not been noted.

Kernel:

*Length*.—On average, about 19.0 to about 21.0 mm.

*Width*.—On average, about 13.0 to about 15.0 mm.

*Thickness*.—On average, about 5.0 to about 6.0 mm.

*Size*.—The kernel is considered medium in size.

*Form*.—Considered generally ovoid.

*Kernel surface texture*.—The kernel pellicle is considered to be slightly pubescent.

*Color*.—A dark tan (RHS Greyed-Orange Group 165 B).

Use: The present variety 'Burpeachfortytwo' is considered to be a peach tree of the late season of maturity, and which produces fruit which are considered to be firm, attractively colored, and which are useful for both local and long distance shipping.

Keeping quality: Considered to be excellent for the species. The fruit of the present variety has stored well for periods of up to 35 days after harvest at 1.0 degree Celsius.

Shipping quality: Considered to be good for the species. The fruit of the new peach tree variety showed minimal bruising of the flesh or skin damage after being subjected to normal harvesting and packing procedures.

Resistance to insects and disease: No particular susceptibilities or resistances were noted. The present variety has not been intentionally tested to expose or detect any susceptibilities or resistances to any known plant, fruit diseases, insect, frost, winter injury, or other environmental factors.

Although the new variety of peach tree possesses the described characteristics when grown under the ecological conditions prevailing near Fowler, Calif., in the central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new distinct variety of peach tree, substantially as illustrated and described, and which is characterized principally as to novelty by producing an attractively colored white-fleshed, clingstone peach which is mature for harvesting and shipment approximately September 5 to September 10 under the ecological conditions prevailing in the San Joaquin Valley of central California.

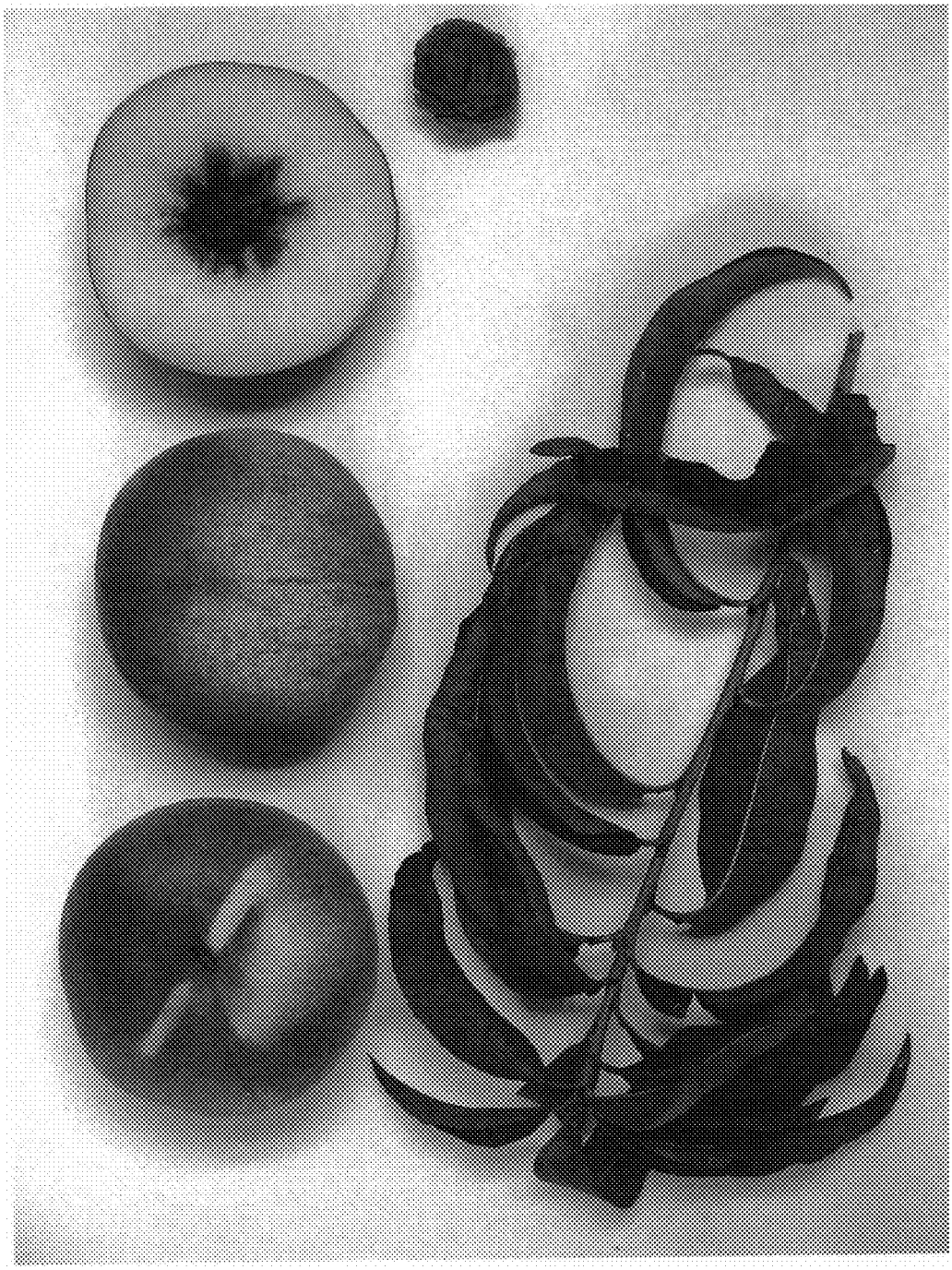

* * * * *